United States Patent [19]

Smeltzer

[11] Patent Number: 5,064,371
[45] Date of Patent: Nov. 12, 1991

[54] DENTAL IMPRESSION TRAY

[76] Inventor: Marsha F. Smeltzer, 4010 Fairway, Port Huron, Mich. 48060

[21] Appl. No.: 675,409

[22] Filed: Mar. 26, 1991

[51] Int. Cl.$^5$ .............................................. A61C 9/00
[52] U.S. Cl. ...................................................... 433/37
[58] Field of Search ......................... 433/37, 41, 45, 47

[56] References Cited

U.S. PATENT DOCUMENTS 1,509,377  6/1920  Rodgers ................................ 433/37
3,690,004  9/1972  Frush ..................................... 433/37

FOREIGN PATENT DOCUMENTS 119154  9/1918  United Kingdom ................. 433/37

Primary Examiner—John J. Wilson
Assistant Examiner—Cindy A. Cherichetti
Attorney, Agent, or Firm—Barnes, Kisselle, Raisch, Choate, Whittemore & Hulbert

[57] ABSTRACT

A dental impression tray particularly for the lower jaw which is designed with arcuate outer walls for the buccal side of the dental arch to locate the arch and has inner lingual walls angled to encircle and avoid contact with any tori growths within the dental arch, thus allowing the tray filled with soft and hardenable material to seat well within the dental arch to obtain a full tooth impression down to and below the gum line.

1 Claim, 1 Drawing Sheet

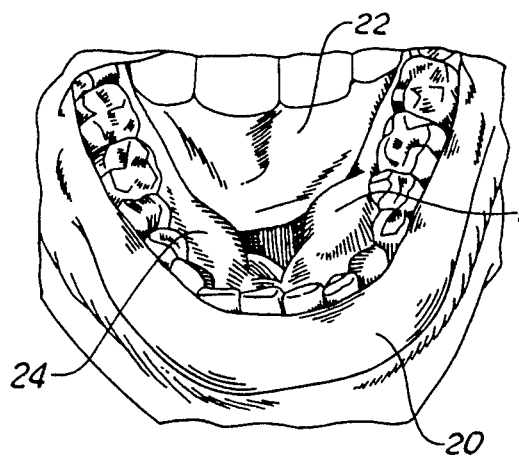
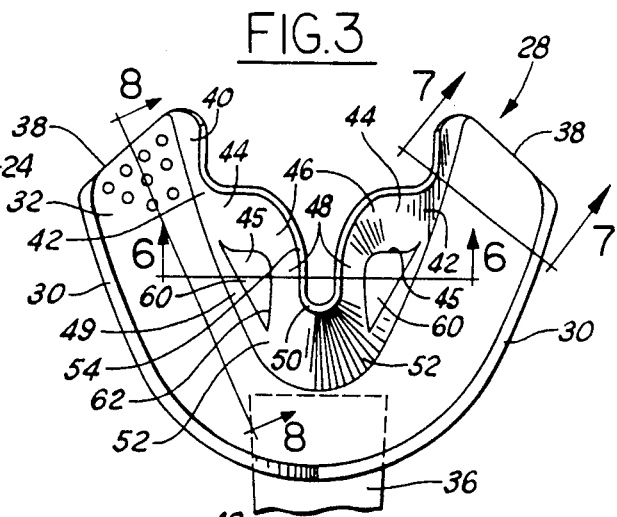
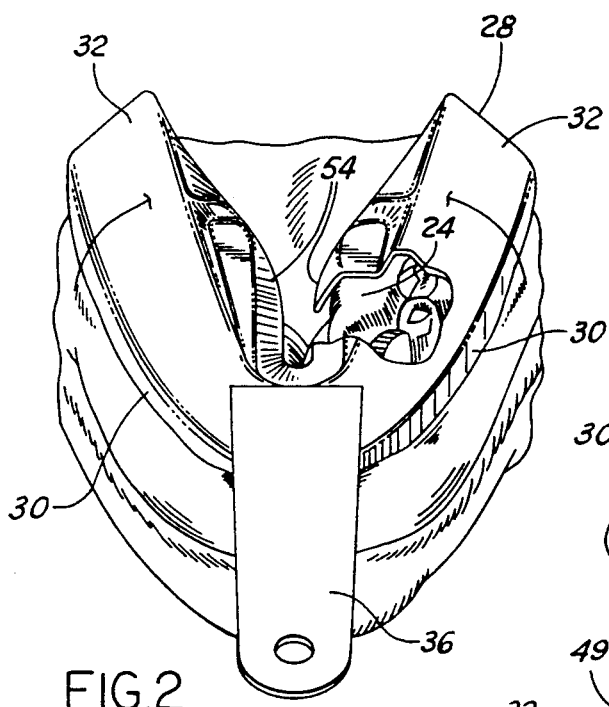
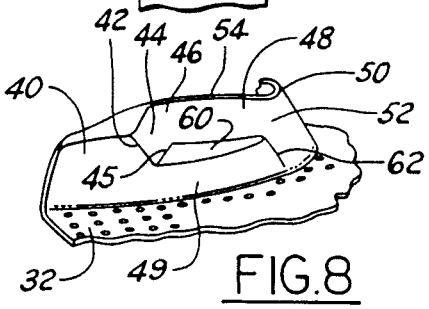
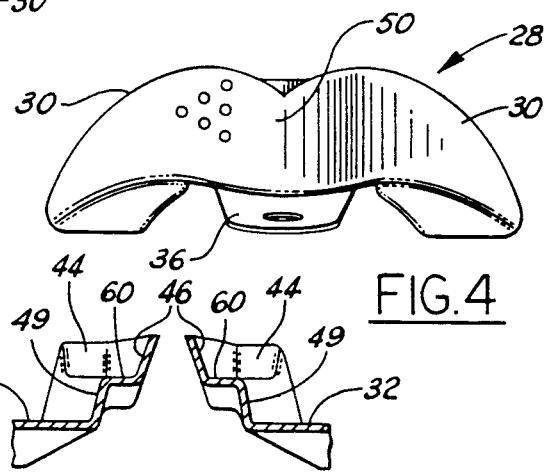
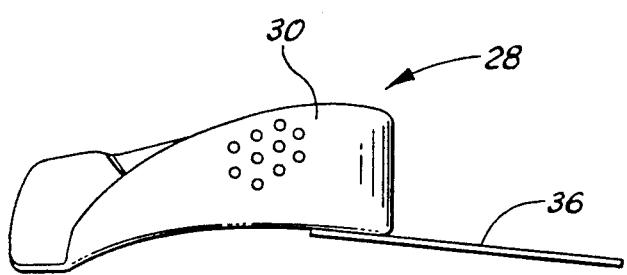
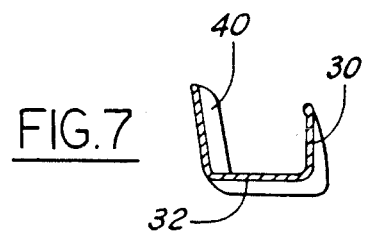

DENTAL IMPRESSION TRAY

FIELD OF INVENTION

Dental trays which are filled with a soft material and applied to an upper or lower tooth formation in the human mouth to obtain an accurate impression of a tooth relationship for purposes of preparation of tooth crowns and other diagnostic purposes.

BACKGROUND AND FEATURES OF THE INVENTION

Arcuate dental trays have been used for many years to obtain an accurate impression of a tooth formation or a gum contour preparatory to dental repair, replacement or orthodontia. Often the use of these trays, which must be pressed down in the mouth with considerable pressure, cause patient discomfort. In many cases, this discomfort is caused by the presence of what is termed a growth in the mouth called torus mandibularis, slow growing bony protuberances or exostoses which are found on the lingual surface of the lower jaw or mandible, opposite the bicuspid teeth. These occur bilaterally on both sides of the jaw adjacent to the tongue, most usually on the lingual side, and may vary in size or shape. In some cases, the tori mandibularis is unilateral on one side only.

Whether unilateral or bilateral, when a filled standard impression tray is inserted in the mouth and pressed down to obtain an impression of the teeth in the lower jaw, the lower edges of the standard tray will strike the torus mandibularis and cause considerable discomfort. This may also inhibit proper placement of the tray and interfere with the obtaining of a proper and accurate impression.

It is an object of the present invention to provide a dental impression tray which can be used for patients with or without the torus mandibularis. The trays may be made of perforated metal, hydrocolloid, plastic disposable material or cast metal and may be made in different lengths and widths. The lingual and buccal flanges which pass on each side of the dental arch are modified so that the lingual walls are brought closely together into the center of the mandible and thus avoid direct contact with the tori. The outer buccal walls of the tray will center the tray properly, thus placing the lingual walls in a position to avoid contact with the existing tori.

Other objects and features of the invention will be apparent in the following description and claims in which the principles of the invention are set forth together with details to enable persons skilled in the art to practice the invention, all in connection with the best mode presently contemplated for the invention.

BRIEF DESCRIPTION OF THE DRAWINGS

DRAWINGS accompany the disclosure and the various views thereof may be briefly described as:

FIG. 1, an occlusal view of the mandible illustrating the location of the tori.

FIG. 2, a view of a tray shaped according to the present invention and in an impression position on the lower jaw.

FIG. 3, a view of the lower impression surface of the tray.

FIG. 4, a front view of the modified tray in inverted position.

FIG. 5, a side view of the tray in inverted position.

FIG. 6, a sectional view of the tray taken on line 6—6 of FIG. 3.

FIG. 7, a sectioned view of the tray on line 7—7 of FIG. 3.

FIG. 8, a sectional view on line 8—8 of FIG. 3.

DETAILED DESCRIPTION OF THE DRAWINGS

In FIG. 1, a view of a mandibular arch of the teeth is shown inside the lips 20. The tongue 22 is raised to show the tori mandibularis 24 inside the dental arch adjacent to the teeth. It will be seen that a standard impression tray which follows the inner and outer contours of the mandibular arch would bear down on the tori and cause pain and discomfort. This would prevent full downward placement of the tray and interfere with a complete impression reaching to the floor of the mouth and full vestibular depth.

In FIG. 2, a similar view shows the improved tray 28 of the present invention in position to take an impression of the mandibular arch. The outer wall 30 of the tray is fashioned to lie essentially at right angles to the plane of the base and to fit around the outside of the teeth, that is, the buccal side.

In FIG. 3, the tray 28 is shown in an inverted position. The arcuate side walls 30 are illustrated rising at right angles from an arcuate base wall 32. A placement handle 36 is fastened to the bight of the base 32. The ends 38 of the arcuate base are angled outwardly and forwardly as shown in the drawing.

The invention lies in the inner wall of the impression tray which rises from the inner edge of the arcuate base 32. Adjacent the ends of the base wall, the lingual walls 40 rise at an angle 10° to 15° and extend to a rounded corner 42 where the inner wall turns toward the axis of the tray in a planar portion 44. This portion then sweeps inwardly from the portions 44 in a curved wall 46 to parallel sections 48 which join in a connection bight 50. The lower and longer portion 49 of the back walls 40 as viewed in FIG. 8 at the area adjacent the base wall 32 sweeps forward to the bight area 50 which has walls 52 rising at an angle from the base 32 to the smallest dimension of the bight 50 with edges 54 sweeping inwardly.

Forward of the planar portion 44 is a ledge 60 roughly triangular in shape which merges with the portion 44 in a curved fillet 45 and extends forward to a merging line 62 just short of the bight area 50 (FIG. 8). In FIG. 7, the section 7—7 of FIG. 3 shows the angle relationship of the base 32, the outer wall 30 and the inner wall 40. In FIG. 8, a partial section illustrates the inner wall from the rear of the base plate to the bight 50 showing the ledge 60.

The converging walls 44, 46 and 48 not only bring the inward edges 54 to a position to overlie the tori but the angle of the inner walls also moves the impression material toward the teeth and gums on the lingual side to provide a tight impression.

Thus, it will be seen, in FIGS. 2 and 3, that the edges 54 of the inner walls span and override the tori 24 and thus will not block the downward progression of the tray as it is pressed into the mandibular arch.

The described impression tray will improve the quality and delivery of dental care from both the practitioner's and the patient's point of view. It will diminish the likelihood of having to make repeat impressions or of having to make post-delivery adjustments following prosthetic placement. The greater comfort can result in better patient acceptance of the required procedures.

It will be appreciated that the trays can be made in differing sizes to accommodate the smaller arch of children and possible sizes intermediate the smallest and the full adult size.

What is claimed is:

1. A mandibular impression tray for use in dental procedures which comprises a unitary piece including an arched base wall having a central bight and ends at the respective ends of the arch, an outer buccal wall surrounding the outer rim of the base wall disposed essentially at right angles to the base wall, inner containment walls extending from the respective ends of the base arch to the bight of the arched base each comprising:

(a) a first rearward section rising upwardly and inwardly at a small angle from the base wall and facing the buccal wall, (b) an intermediate section forward of the rearward section and rising from the base wall about half the distance of the first rearward section and terminating close to the bight of the arched base, (c) a ledge extending inwardly from the top of the intermediate section spaced above the base wall and terminating approximately at the end of the intermediate section, and (d) inner containment walls above said ledge curving inwardly from said first rearward section inside said ledges to a narrowed bight with top edges sweeping from a wide rearward area to a narrowed forward area terminating at said narrowed bight, and (e) said bight extending from said base and to said narrowed bight at a rising angle toward the rear of the tray.

* * * * *